(12) United States Patent
Fleute-Schlachter et al.

(10) Patent No.: US 9,107,403 B2
(45) Date of Patent: Aug. 18, 2015

(54) AGROCHEMICAL AUXILIARY COMPOSITIONS

(75) Inventors: Ingo Fleute-Schlachter, Essen (DE); Stéphanie Merlet, Le Celle sur Morin (FR); Klaus Jürgen Baldauf, Sao José dos Campos (BR); Hans-Georg Mainx, Leichlingen (DE); Benoit Abribat, Aubervilliers Cedex (FR)

(73) Assignee: Cognis IP Management GmbH, Duesseldorf (DE)

( * ) Notice: Subject to any disclaimer, the term of this patent is extended or adjusted under 35 U.S.C. 154(b) by 454 days.

(21) Appl. No.: 13/141,463

(22) PCT Filed: Dec. 12, 2009

(86) PCT No.: PCT/EP2009/008899
§ 371 (c)(1),
(2), (4) Date: Jun. 22, 2011

(87) PCT Pub. No.: WO2010/072341
PCT Pub. Date: Jul. 1, 2010

(65) Prior Publication Data
US 2011/0257234 A1 Oct. 20, 2011

Related U.S. Application Data

(60) Provisional application No. 61/140,429, filed on Dec. 23, 2008.

(51) Int. Cl.
| | | |
|---|---|---|
| *A01N 43/653* | (2006.01) | |
| *A01N 43/56* | (2006.01) | |
| *A01P 3/00* | (2006.01) | |
| *A01N 25/00* | (2006.01) | |
| *A01N 25/30* | (2006.01) | |
| *A01N 47/24* | (2006.01) | |
| *A01N 47/36* | (2006.01) | |

(52) U.S. Cl.
CPC ............ *A01N 25/30* (2013.01); *A01N 43/653* (2013.01); *A01N 47/24* (2013.01); *A01N 47/36* (2013.01)

(58) Field of Classification Search
CPC ....... A01N 65/00; A01N 25/04; A01N 53/00; A01N 25/34; A61Q 17/005
See application file for complete search history.

(56) References Cited

U.S. PATENT DOCUMENTS

| | | | |
|---|---|---|---|
| 6,103,770 A | 8/2000 | Trouve | |
| 6,764,979 B2 | 7/2004 | Wollenweber et al. | |
| 7,585,830 B2 | 9/2009 | Behler et al. | |
| 2007/0032382 A1* | 2/2007 | Volgas et al. | 504/101 |
| 2007/0213226 A1* | 9/2007 | Sieverding et al. | 504/206 |
| 2010/0190648 A1* | 7/2010 | Tollington et al. | 504/234 |
| 2011/0132466 A1* | 6/2011 | Bucher | 137/13 |

FOREIGN PATENT DOCUMENTS

| | | |
|---|---|---|
| CA | 2396051 | 7/2001 |
| DE | 268147 | 5/1989 |
| DE | 10000320 | 7/2001 |
| DE | 10018159 | 10/2001 |
| EP | 0804241 | 11/1997 |
| EP | 1045021 | 10/2000 |
| EP | 1716163 | 4/2008 |
| WO | WO-98/09518 | 3/1998 |
| WO | 02/069705 | 9/2002 |

OTHER PUBLICATIONS

Czichocki, Gunther et al., Characterization of alkyl polyglycosides by both reversed-phase and normal-phase modes of high-performance liquid chromatography, Journal of Chromatography A, 943, 2003, pp. 241-250.*
O'Neil, Maryadele J. et al., The Merck Index—An Encyclopedia of Chemicals, Drugs, and Biologicals (14th Edition—Version 14.9), 2006, 2012.*
Czichocki, Gunther et al., Characterization of alkyl polyglycosides by both reversed-phase and normal-phase modes of high-performance liquid chromatography, Journal of Chomatography A, 943, 2003, pp. 241-250.*
Haefs et al., Studies on a new group of biodegradable surfactants for glyphosate, Pest Manag. Sci., 2002, 58, pp. 825-833.*
Kramer, Deposit Characteristics, Penetration and Biological Efficacy of Selected Agrochemicals as Affected by Surfactants and Plant Micromorphology, 2009, p. 10.*
International Search Report, PCT/EP2009/008899 dated Aug. 16, 2011, pp. 1-9.

* cited by examiner

*Primary Examiner* — San-Ming Hui
*Assistant Examiner* — Andrew Lee
(74) *Attorney, Agent, or Firm* — Servilla Whitney LLC

(57) ABSTRACT

Suggested are agrochemical auxiliary compositions, comprising (a) alkoxylated polyol esters, (b) optionally alkoxylated alk(en)yl oligoglycosides, and (c) fatty acids or their salts.

16 Claims, No Drawings

AGROCHEMICAL AUXILIARY COMPOSITIONS

CROSS-REFERENCE TO RELATED APPLICATIONS

This application is the national stage entry of PCT/EP2009/008899, filed on Dec. 12, 2009, which claims priority to U.S. Provisional Patent application No. 61/140,429, filed on Dec. 23, 2008, both of which are incorporated herein by reference in their entireties.

FIELD OF THE INVENTION

The present invention is related to the area of agriculture and refers to new auxiliary compositions comprising non-ionic surfactants and soaps.

BACKGROUND OF THE INVENTION

The crop protection market represents a total value of around € 22 billion/year. Most biocides are formulated with adjuvants (also known as potentiators) to maximise their efficacy by fulfilling several functions. An adjuvant must provide good wetting of the leaf surface, facilitate the foliar penetration of the biocide under a wide range of climatic conditions and enhance, or at least not inhibit, translocation of the biocide, in particular the herbicide into the plant. In addition, it must not produce phytotoxic effects when used on specific resistant crops.

The use of ethoxylated vegetable oils as additives for biocide and plant protection formulations represents a well known state of the art. One of the first references describing ethoxylated triglycerides for this purpose has been a laid-open publication from earlier German Democratic Republic DD 268147 A1. In this context also reference is made to international patent application WO 98/009518 A1 (Cognis) disclosing agricultural composition comprising a liquid carrier and an emulsifier mixture consisting of alkyl polyglucosides and fatty acids. From the two German applications DE 100 00 320 A1 and DE 100 18 159 A1 (both Cognis) compositions are known comprising certain contact herbicides and ethoxylated fatty alcohols or fatty acids. European patent EP 0804241 B1 (SEPPIC) refers to ethoxylated fatty acid esters and triglycerides and their use as auto-emulsifiable systems for making agricultural compositions.

Although various types of biocides and also a huge number of additives, like adjuvants, emulsifiers, solubilisers and the like are available in the market, there is constant desire to develop new auxiliary agents increasing the speed of penetration of actives into the leaves of the plants to be protected and improving the ability of the actives to fight different microorganisms, especially all kinds of fungi. It has been the object of the present invention to comply with these needs of the market.

SUMMARY OF THE INVENTION

One aspect of the invention relates to an agrochemical auxiliary composition comprising an alkoxylated polyol ester, optionally an alkoxylated alkyl or alkenyl oligoglycoside and a fatty acid or salt thereof. Another aspect of the invention relates to an agrochemical composition comprising an alkoxylated polyol ester, optionally an alkoxylated alk(en)yl oligoglycoside, a fatty acid or salt thereof, and a biocide. A final aspect of the invention relates to a method of producing agrochemical compositions comprising using said agrochemical auxiliary compositions as emulsifiers, adjuvants, solvents, solubilizers or tank-mix additives.

DETAILED DESCRIPTION OF THE INVENTION

The present invention refers to new agrochemical auxiliary compositions, comprising
(a) alkoxylated polyol esters,
(b) optionally alkoxylated alk(en)yl oligoglycosides
(c) fatty acids or their salts.

It has been observed that mixtures comprising alkoxylated polyol esters, optionally alkoxylated alk(en)yl oligoglycosides and fatty acids or their salts increase efficiency of various types of biocides, namely fungicides, insecticides, herbicides and plant growth regulators. Although it has been known for quite a while that for example alkoxylated triglycerides stimulate penetration of systemic biocides into the leaves, it has now surprisingly been found that adding glycosides and fatty acids to these known surfactants does not only increase speed of penetration into leaves in general, but also allows the penetration of cell walls of fungi.

Alkoxylated Polyol Esters

Alkoxylated polyol esters (component a) represent the major part of the auxiliary composition. These esters may be derived from trimethylol propane, pentaerytrol or preferably from glycerol. Esters according to the present invention encompass full and partial esters. For example, suitable alkoxylated glycerol esters include alkoxylated mono-, di- or tri glycerides or their mixtures. Alkoxylated triglycerides—or used as a synonym alkoxylated vegetable oils—represent the by far most preferred compounds and are typically following general formula (I)

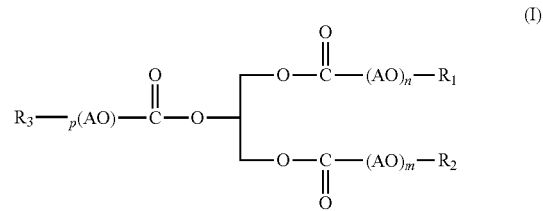

in which $R^1$, $R^2$ and $R^3$ independently from each other represent linear or branched, saturated or unsaturated alkyl and/or hydroxy alkyl residues having 5 to 21, preferably 11 to 17 carbon atoms; n, m and p independently from each other stand for 0 or integers of from about 1 to about 50, preferably about 3 to about 30 and most preferably about 5 to about 15 with the condition that the sum (m+n+p) is different from zero, and AO represents an ethylene glycol or propylene glycol unit. In a preferred embodiment said alkoxylated glycerol esters are derived from soybean oil, rapeseed oil, sunflower oil or linseed oil, although other vegetable oils not mentioned here may also form a suitable basis for the components.

Alkoxylation of the polyol esters is conducted according to standard processes known in organic chemistry. Typically, ethylene oxide, propylene oxide or their mixtures are added to the esters in the presence of an alkaline catalyst. Since alkoxylation represents a statistical reaction the reaction products show a distribution of homologues having different degrees of alkoxylation. In this context it should be clear that a given degree of alkoxylation always represents an average value. It is possible to control alkoxylation by selecting an adequate catalyst for obtaining either a broad or narrow homologue distribution. Nevertheless, both types of products are suitable, although an alkoxylate having a lower degree of alkoxylation but a broader homologue distribution may show a similar behaviour like another alkoxylate having a higher alkoxylation degree, but a narrow-range distribution of homologues. It is also possible to use mixed products comprising ethylene oxide and propylene oxide units, either blockwise or randomised. The most preferred species, however, are adducts of about 10 mol ethylene oxide to soybean oil, rapeseed oil or linseed oil. It is also possible to define the alkoxylated polyol esters in general and the alkoxylated glycerides in particular by their HLB value, which can be calculated according to the following equation $$HLB=20[1-S/A]$$

in which "S" stands for the saponification number of the alkoxylated ester (according to NFT 60206) and "A" represents the acid number of the acid used for esterification (according to NFT 60204). Preferred alkoxylated polyol esters exhibit HLB values in the range of about 2 to about 15 and preferably about 4 to about 10.

Alk(En)Yl Oligoglycosides and their Alkoxylation Products

The alkyl or alkenyl oligoglycosides (component b1) which can be used in the compositions according to the invention as component (II) may be derived from aldoses or ketoses containing 5 or 6 carbon atoms, preferably glucose. Accordingly, the preferred alkyl and/or alkenyl oligoglycosides are alkyl or alkenyl oligoglucosides. These materials are also known generically as "alkyl polyglycosides" (APG). The alk(en)yl oligoglycosides according to the invention correspond to formula (II):

$$R^4O[G]_p \quad (II)$$

wherein $R^4$ is an alkyl or alkenyl radical having from 6 to 22 carbon atoms, G is a sugar unit having 5 or 6 carbon atoms and p is a number from 1 to 10. The index p in general formula (II) indicates the degree of oligomerisation (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is mostly a broken number. Alk(en)yl oligoglycosides having an average degree of oligomerisation p of 1.1 to 3.0 are preferably used. Alk(en)yl oligoglycosides having a degree of oligomerisation below 1.7 and, more particularly, between 1.2 and 1.4 are preferred from the applicational point of view.

The alkyl or alkenyl radical $R^4$ may be derived from primary alcohols containing 4 to 22 and preferably 8 to 18 carbon atoms. Typical examples are butanol, caproic alcohol, caprylic alcohol, capric alcohol, undecyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof such as are formed, for example, in the hydrogenation of technical fatty acid methyl esters or in the hydrogenation of aldehydes from Roelen's oxo synthesis. Alkyl oligoglucosides based on short chain $C_{8/10}$ fatty alcohols or hydrogenated $C_{8/18}$ coconut oil alcohols having a DP of 1 to 3 are preferred.

Suitable alternatives instead of said alk(en)yl oligoglycosides are their alkoxylation products (component b2). These surfactants are obtainable by adding about 1 to about 20, preferably about 2 to about 15 and more preferably about 3 to about 10 mol ethylene oxide (EO) and/or propylene oxide (PO)—either blockwise or random—to the free hydroxyl groups of the glycoside body. Particularly preferred are adducts of about 2 to about 7 mol EO and/or PO to $C_{8/10}$- or respectively $C_{12/14}$ alkyl oligoglucosides. As far as the manufacture of these surfactants is concerned reference is made to EP 1716163 B1 (Cognis) disclosing one suitable production process.

Fatty Acids and their Salts

Fatty acids and their salts (component c) improve behaviour and stability of the formulation. Typically they follow general formula (III)

$$R^5CO\text{—}OX \quad (III)$$

in which $R^5CO$ represents a linear or branched, saturated or unsaturated acyl radical having 6 to 22, preferably 12 to 18 carbon atoms and X stands for hydrogen or an alkaline metal. Suitable examples are capronic acid, caprylic acid, caprinic acid, lauric acid, myristic acid, palmitic acid, palmoleic acid, stearic acid, oleic acid, lineoleic acid, conjugated linoleic acid, linolenic acid, arachidonic acid, gadoleinic acid, behenic acid, erucic acid and their technical mixtures like for example coco fatty acid, tallow fatty acid or preferably tall oil fatty acid. Instead of the acids one can also use the respective sodium or potassium soaps.

Auxiliary Compositions

In a preferred embodiment the auxiliary compositions according to the present invention may comprise
(a) about 60 to about 90, preferably about 70 to about 80% w/w alkoxylated polyol esters
(b) about 5 to about 15, preferably about 7 to about 12% w/w optionally alkoxylated alk(en)yl oligoglycosides, and
(c) about 5 to about 15, preferably about 7 to about 12% w/w fatty acids or their salts
under the conditions that the values add optionally together with water to 100% w/w.

INDUSTRIAL APPLICATION

Agrochemical Compositions

Another object of the present invention refers to agrochemical compositions comprising
(a) alkoxylated polyol esters,
(b) optionally alkoxylated alk(en)yl oligoglycosides,
(c) fatty acids or their salts, and
(d) biocides.

Typically, said agrochemical auxiliary compositions comprising the components (a), (b) and (c) are placed in the formed of aqueous solutions and the respective biocides dissolved therein. According to the needs of the customer, concentrates thus obtained—comprising typically up to 40% w/w biocides—are diluted in place to a ready-to-use composition showing a biocide concentration of about 0.5 to about 1% w/w.

Biocides

A biocide in the context of the present invention is a plant protection agent, more particular a chemical substance capable of killing different forms of living organisms used in fields such as medicine, agriculture, forestry, and mosquito control. Also counted under the group of biocides are so-called plant growth regulators. Usually, biocides are divided into two subgroups:
 pesticides, which includes fungicides, herbicides, insecticides, algicides, moluscicides, miticides and rodenticides, and
 antimicrobials, which includes germicides, antibiotics, antibacterials, antivirals, antifungals, antiprotozoals and antiparasites.

Biocides can also be added to other materials (typically liquids) to protect the material from biological infestation and growth. For example, certain types of quaternary ammonium compounds (quats) can be added to pool water or industrial water systems to act as an algicide, protecting the water from infestation and growth of algae.

Pesticides

The U.S. Environmental Protection Agency (EPA) defines a pesticide as "any substance or mixture of substances intended for preventing, destroying, repelling, or mitigating any pest". A pesticide may be a chemical substance or biological agent (such as a virus or bacteria) used against pests including insects, plant pathogens, weeds, mollusks, birds, mammals, fish, nematodes (roundworms) and microbes that compete with humans for food, destroy property, spread disease or are a nuisance. In the following examples, pesticides suitable for the agrochemical compositions according to the present invention are given:

Fungicides.

A fungicide is one of three main methods of pest control—the chemical control of fungi in this case. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies. Examples for suitable fungicides, according to the present invention, encompass the following species: (3-ethoxypropyl)mercury bromide, 2-methoxyethylmercury chloride, 2-phenylphenol, 8-hydroxyquinoline sulfate, 8-phenylmercurioxyquinoline, acibenzolar, acylamino acid fungicides, acypetacs, aldimorph, aliphatic nitrogen fungicides, allyl alcohol, amide fungicides, ampropylfos, anilazine, anilide fungicides, antibiotic fungicides, aromatic fungicides, aureofungin, azaconazole, azithiram, azoxystrobin, barium polysulfide, benalaxyl benalaxyl-M, benodanil, benomyl, benquinox, bentaluron, benthiavalicarb, benzalkonium chloride, benzamacril, benzamide fungicides, benzamorf, benzanilide fungicides, benzimidazole fungicides, benzimidazole precursor fungicides, benzimidazolylcarbamate fungicides, benzohydroxamic acid, benzothiazole fungicides, bethoxazin, binapacryl, biphenyl, bitertanol, bithionol, blasticidin-S, Bordeaux mixture, boscalid, bridged diphenyl fungicides, bromuconazole, bupirimate, Burgundy mixture, buthiobate, butylamine, calcium polysulfide, captafol, captan, carbamate fungicides, carbamorph, carbanilate fungicides, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper(II) acetate, copper(II) carbonate, basic, copper fungicides, copper hydroxide, copper naphthenate, copper oleate, copper oxychloride, copper(II) sulfate, copper sulfate, basic, copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dicarboximide fungicides, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, dinitrophenol fungicides, dinobuton, dinocap, dinocton, dinopenton, dinosulfon, dinot-erbon, diphenylamine, dipyrithione, disulfuram, ditalimfos, dithianon, dithiocarbamate fungicides, DNOC, dodemorph, dodicin, dodine, DONATODINE, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, fludioxonil, flumetover, flumorph, fluopicolide, fluoroimide, flutriazole, fluoxastrobin, fluquinconazole, flusilazole, flusulfamide, flutolanil, flutriafol, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hymexazol, imazalil, imibenconazole, imidazole fungicides, iminoctadine, inorganic fungicides, inorganic mercury fungicides, iodomethane, ipconazole, iprobenfos, iprodione, iprovalicarb, isoprothiolane, isovaledione, kasugamycin, kresoxim-methyl, lime sulphur, mancopper, mancozeb, maneb, mebenil, mecarbinzid, mepanipyrim, mepronil, mercuric chloride, mercuric oxide, mercurous chloride, mercury fungicides, metalaxyl, metalaxyl-M, metam, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, morpholine fungicides, myclobutanil, myclozolin, N-(ethylmercury)-p-toluenesulphonanilide, nabam, natamycin, nitrostyrene, nitrothalisopropyl, nuarimol, OCH, octhilinone, ofurace, organomercury fungicides, organophosphorus fungicides, organotin fungicides, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulfamide fungicides, phosdiphen, phthalide, phthalimide fungicides, picoxystrobin, piperalin, polycarbamate, polymeric dithiocarbamate fungicides, polyoxins, polyoxorim, polysulfide fungicides, potassium azide, potassium polysulfide, potassium thiocyanate, probenazole, prochloraz, procymidone, propamocarb, propiconazole, propineb, proquinazid, prothiocarb, prothioconazole, pyracarbolid, pyraclostrobin, pyrazole fungicides, pyrazophos, pyridine fungicides, pyridinitril, pyrifenox, pyrimethanil, pyrimidine fungicides, pyroquilon, pyroxychlor, pyroxyfur, pyrrole fungicides, quinacetol, quinazamid, quinconazole, quinoline fungicides, quinone fungicides, quinoxaline fungicides, quinoxyfen, quintozene, rabenzazole, salicylanilide, silthiofam, simeconazole, sodium azide, sodium orthophenylphenoxide, sodium pentachlorophenoxide, sodium polysulfide, spiroxamine, streptomycin, strobilurin fungicides, sulfonanilide fungicides, sulfur, sultropen, TCMTB, tebuconazole, tecloftalam, tecnazene, tecoram, tetraconazole, thiabendazole, thiadifluor, thiazole fungicides, thicyofen, thifluzamide, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, tridemorph, trifloxystrobin, triflumizole, triforine, triticonazole, unclassified fungicides, undecylenic acid, uniconazole, urea fungicides, validamycin, valinamide fungicides, vinclozolin, zarilamid, zinc naphthenate, zineb, ziram, zoxamide and their mixtures.

Herbicides.

An herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are nonselective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat. In general, active ingredients representing various chemical classes can be used, here specific reference is made to the The Pesticide Manual, Fourteenth edition, ed. CDS Tomlin, BCPC 2006. The following selection illustrates examples, which are by no means limitation to this invention: aryloxycarboxylic acid e.g. MCPA, aryloxyphenoxypropionates e.g. clodinafop, cyclohexanedione oximes e.g. sethoxydim, dinitroanilines e.g. trifluralin, diphenyl ethers e.g. oxyfluorfen, hydroxybenzonitriles e.g. bromoxynil, sulfonyureas e.g. nicosulfuron, triazolopyrimidines e.g. penoxsulam, triketiones e.g. mesotriones, ureas e.g. diuron. In the following, a number of specifically suitable herbicides are compiled:

- 2,4-D, a broadleaf herbicide in the phenoxy group used in turf and in no-till field crop production. Now mainly used in a blend with other herbicides that act as synergists, it is the most widely used herbicide in the world, third most commonly used in the United States. It is an example of synthetic auxin (plant hormone).
- Atrazine, a triazine herbicide used in corn and sorghum for control of broadleaf weeds and grasses. It is still used because of its low cost and because it works as a synergist when used with other herbicides, it is a photosystem II inhibitor.
- Dicamba as benzoic acid, a persistent broadleaf herbicide active in the soil, used on turf and field corn. It is another example of synthetic auxin.
- Glyphosate, a systemic nonselective (it kills any type of plant) herbicide used in no-till burndown and for weed control in crops that are genetically modified to resist its effects. It is an example of a EPSPs inhibitor.
- Imazapic as imidazolinone, a selective herbicide for both the pre- and post-emergent control of some annual and perennial grasses and some broadleaf weeds. Imazapic kills plants by inhibiting the production of branched chain amino acids (valine, leucine, and isoleucine), which are necessary for protein synthesis and cell growth.
- Metolachlor as chloroacetamide, a pre-emergent herbicide widely used for control of annual grasses in corn and sorghum; it has largely replaced atrazine for these uses.
- Paraquat as bypyridylium, a nonselective contact herbicide used for no-till burndown and in aerial destruction of marijuana and coca plantings. More acutely toxic to people than any other herbicide in widespread commercial use.
- Picloram, clopyralid, and triclopyr as pyridinecarboxylic acids or synthetic auxins, used to control unwanted woody plants and broad-leaved weeds.

Insecticides.

An insecticide is a pesticide used against insects in all developmental forms. They include ovicides and larvicides used against the eggs and larvae of insects. Insecticides are used in agriculture, medicine, industry and the household. In the following, suitable insecticides are mentioned:

- Chlorinated insecticides such as, for example, Camphechlor, DDT, Hexachlorocyclohexane, gamma-Hexachlorocyclohexane, Methoxychlor, Pentachlorophenol, TDE, Aldrin, Chlordane, Chlordecone, Dieldrin, Endosulfan, Endrin, Heptachlor, Mirex and their mixtures;
- Organophosphorus compounds such as, for example, Acephate, Azinphos-methyl, Bensulide, Chlorethoxyfos, Chlorpyrifos, Chlorpyriphos-methyl, Diazinon, Dichlorvos (DDVP), Dicrotophos, Dimethoate, Disulfoton, Ethoprop, Fenamiphos, Fenitrothion, Fenthion, Fosthiazate, Malathion, Methamidophos, Methidathion, Methyl-parathion, Mevinphos, Naled, Omethoate, Oxydemeton-methyl, Parathion, Phorate, Phosalone, Phosmet, Phostebupirim, Pirimiphos-methyl, Profenofos, Terbufos, Tetrachlorvinphos, Tribufos, Trichlorfon and their mixture;
- Carbamates such as, for example, Aldicarb, Carbofuran, Carbaryl, Methomyl, 2-(1-Methylpropyl)phenyl methylcarbamate and their mixtures;
- Pyrethroids such as, for example, Allethrin, Bifenthrin, Deltamethrin, Permethrin, Resmethrin, Sumithrin, Tetramethrin, Tralomethrin, Transfluthrin and their mixtures;
- Plant toxin derived compounds such as, for example, Derris (rotenone), Pyrethrum, Neem (Azadirachtin), Nicotine, Caffeine and their mixtures.
- Neonicotinoids such as imidacloprid.
- Abamectin e.g. emamactin
- Oxadiazines such as indoxacarb
- Anthranilic diamides such as rynaxypyr Rodenticides.

Rodenticides are a category of pest control chemicals intended to kill rodents. Rodents are difficult to kill with poisons because their feeding habits reflect their place as scavengers. They would eat a small bit of something and wait, and if they do not get sick, they would continue eating. An effective rodenticide must be tasteless and odorless in lethal concentrations, and have a delayed effect. In the following, examples for suitable rodenticides are given:

- Anticoagulants are defined as chronic (death occurs after 1-2 weeks post ingestion of the lethal dose, rarely sooner), single-dose (second generation) or multiple dose (first generation) cumulative rodenticides. Fatal internal bleeding is caused by lethal dose of anticoagulants such as brodifacoum, coumatetralyl or warfarin. These substances in effective doses are antivitamins K, blocking the enzymes $K_1$-2,3-epoxide-reductase (this enzyme is preferentially blocked by 4-hydroxycoumarin/4-hydroxythiacoumarin derivatives) and $K_1$-quinone-reductase (this enzyme is preferentially blocked by indandione derivatives), depriving the organism of its source of active vitamin $K_1$. This leads to a disruption of the vitamin K cycle, resulting in an inability of production of essential blood-clotting factors (mainly coagulation factors II (prothrombin), VII (proconvertin), IX (Christmas factor) and X (Stuart factor)). In addition to this specific metabolic disruption, toxic doses of 4-hydroxycoumarin/4-hydroxythiacoumarin and indandione anticoagulants are causing damage to tiny blood vessels (capillaries), increasing their permeability, causing diffuse internal bleedings (haemorrhagias). These effects are gradual; they develop in the course of days and are not accompanied by any nociceptive perceptions, such as pain or agony. In the final phase of intoxication the exhausted rodent collapses in hypovolemic circulatory shock or severe anemia and dies calmly. Rodenticidal anticoagulants are either first generation agents (4-hydroxycoumarin type: warfarin, coumatetralyl; indandione type: pindone, diphacinone, chlorophacinone), generally requiring higher concentrations (usually between 0.005 and 0.1%), consecutive intake over days in order to accumulate the lethal dose, poor active or inactive after single feeding and less toxic than second generation agents, which are derivatives of 4-hydroxycoumarin (difenacoum, brodifacoum, bromadiolone and flocoumafen) or 4-hydroxy-1-benzothiin-2-one (4-hydroxy-1-thiacoumarin, sometimes incorrectlly referred to as 4-hydroxy-1-thiocoumarin, for reason see heterocyclic compounds), namely difethialone. Second generation agents are far more toxic than first generation agents, they are generally applied in lower concentrations in baits (usually in the order of 0.001-0.005%), and are lethal after single ingestion of bait and are effective also against strains of rodents that have become resistant against first generation anticoagulants; thus the second generation anticoagulants are sometimes referred to as "superwarfarins". Sometimes, anticoagulant rodenticides are potentiated by an antibiotic, most commonly by sulfaquinoxaline. The aim of this association (e.g. warfarin 0.05%+sulfaquinoxaline 0.02%, or difenacoum 0.005%+sulfaquinoxaline 0.02% etc.) is that the antibiotic/bacteriostatic agent suppresses intestinal/gut symbiotic microflora that represents a source of vitamin K. Thus the symbiotic bacteria are killed or their metabolism is impaired and the production of vitamin K by them is diminished, an effect which logically contributes to the action of anticoagulants. Antibiotic agents other than sulfaquinoxaline may be used, for example co-trimoxazole, tetracycline, neomycin or metronidazole. A further synergism used in rodenticidal baits is that of an association of an anticoagulant with a compound with vitamin D-activity, i.e. cholecalciferol or ergocalciferol (see below). A typical formula used is, e.g., warfarin 0.025-0.05%+cholecalciferol 0.01%. In some countries there are even fixed three-component rodenticides, i.e. anticoagulant+antibiotic+vitamin D, e.g. difenacoum 0.005%+sulfaquinoxaline 0.02%+cholecalciferol 0.01%. Associations of a second-generation anticoagulant with an antibiotic and/or vitamin D are considered to be effective even against the most resistant strains of rodents, though some second generation anticoagulants (namely brodifacoum and difethialone), in bait concentrations of 0.0025-0.005% are so toxic that no known resistant strain of rodents exists and even rodents resistant against any other derivatives are reliably exterminated by application of these most toxic anticoagulants.

Vitamin $K_1$ has been suggested and successfully used as an antidote for pets or humans, which/who were either accidentally or intentionally (poison assaults on pets, suicidal attempts) exposed to anticoagulant poisons. In addition, since some of these poisons act by inhibiting liver functions and in progressed stages of poisoning, several blood-clotting factors as well as the whole volume of circulating blood lacks, a blood transfusion (optionally with the clotting factors present) can save a person's life who inadvertently takes them, which is an advantage over some older poisons.

Metal phosphides have been used as a means of killing rodents and are considered single-dose fast acting rodenticides (death occurs commonly within 1-3 days after single bait ingestion). A bait consisting of food and a phosphide (usually zinc phosphide) is left where the rodents can eat it. The acid in the digestive system of the rodent reacts with the phosphide to generate the toxic phosphine gas. This method of vermin control has possible use in places where rodents are resistant to some of the anticoagulants, particularly for control of house and field mice; zinc phosphide baits are also cheaper than most second-generation anticoagulants, so that sometimes, in cases of large infestation by rodents, their population is initially reduced by copious amounts of zinc phosphide bait applied, and the rest of the population that survived the initial fast-acting poison is then eradicated by prolonged feeding on anticoagulant bait. Inversely, the individual rodents that survived anticoagulant bait poisoning (rest population) can be eradicated by pre-baiting them with nontoxic bait for a week or two (this is important to overcome bait shyness, and to get rodents used to feeding in specific areas by offering specific food, especially when eradicating rats) and subsequently applying poisoned bait of the same sort as used for pre-baiting until all consumption of the bait ceases (usually within 2-4 days). These methods of alternating rodenticides with different modes of action provides a factual or an almost 100% eradication of the rodent population in the area if the acceptance/palatability of bait is good (i.e., rodents readily feed on it).

Phosphides are rather fast acting rat poisons, resulting in that the rats are dying usually in open areas instead of the affected buildings. Typical examples are aluminum phosphide (fumigant only), calcium phosphide (fumigant only), magnesium phosphide (fumigant only) and zinc phosphide (in baits). Zinc phosphide is typically added to rodent baits in amounts of around 0.75-2%. The baits have a strong, pungent garlic-like odor characteristic for phosphine liberated by hydrolysis. The odor attracts (or, at least, does not repulse) rodents, but has a repulsive effect on other mammals; birds, however (notably wild turkeys), are not sensitive to the smell and feed on the bait thus becoming collateral damage.

Hypercalcemia. Calciferols (vitamins D), cholecalciferol (vitamin $D_3$) and ergocalciferol (vitamin $D_2$) are used as rodenticides, which are toxic to rodents for the same reason that they are beneficial to mammals: they are affecting calcium and phosphate homeostasis in the body. Vitamins D are essential in minute quantities (few IUs per kilogram body weight daily, which is only a fraction of a milligram), and like most fat soluble vitamins they are toxic in larger doses as they readily result in the so-called hypervitaminosis, which is, simply said, poisoning by the vitamin. If the poisoning is severe enough (that is, if the dose of the toxicant is high enough), it eventually leads to death. In rodents consuming the rodenticidal bait it causes hypercalcemia by raising the calcium level, mainly by increasing calcium absorption from food, mobilising bone-matrix-fixed calcium into ionised form (mainly monohydrogencarbonate calcium cation, partially bound to plasma proteins, $[CaHCO_3]^+$), which circulates dissolved in the blood plasma, and after ingestion of a lethal dose the free calcium levels are raised sufficiently so that blood vessels, kidneys, the stomach wall and lungs are mineralised/calcificated (formation of calcificates, crystals of calcium salts/complexes in the tissues thus damaging them), leading further to heart problems (myocard is sensitive to variations of free calcium levels that are affecting both myocardial contractibility and excitation propagation between atrias and ventriculas) and bleeding (due to capillary damage) and possibly kidney failure. It is considered to be single-dose, or cumulative (depending on concentration used; the common 0.075% bait concentration is lethal to most rodents after a single intake of larger portions of the bait), sub-chronic (death occurring usually within days to one week after ingestion of the bait). Applied concentrations are 0.075% cholecalciferol and 0.1% ergocalciferol when used alone. There is an important feature of calciferols toxicology which is that they are synergistic with anticoagulant toxicants. This means that mixtures of anticoagulants and calciferols in the same bait are more toxic than the sum of toxicities of the anticoagulant and the calciferol in the bait so that a massive hypercalcemic effect can be achieved by a substantially lower calciferol content in the bait and vice-versa. More pronounced anticoagulant/hemorrhagic effects are observed if calciferol is present. This synergism is mostly used in baits low in calciferol because effective concentrations of calciferols are more expensive than effective concentrations of most anticoagulants. The historically very first application of a calciferol in rodenticidal bait was, in fact, the Sorex product Sorexa® D (with a different formula than today's Sorexa® D) back in the early 1970's, containing warfarin 0.025%+ergocalciferol 0.1%. Today, Sorexa® CD contains a 0.0025% difenacoum+0.075% cholecalciferol combination. Numerous other brand products containing either calciferols 0.075-0.1% (e.g. Quintox®, containing 0.075% cholecalciferol) alone, or a combination of calciferol 0.01-0.075% with an anticoagulant are marketed.

Miticides, moluscicides and nematicides.

Miticides are pesticides that kill mites. Antibiotic miticides, carbamate miticides, formamidine miticides, mite growth regulators, organochlorine, permethrin and organophosphate miticides all belong to this category. Molluscicides are pesticides used to control mollusks, such as moths, slugs and snails. These substances include metaldehyde, methiocarb and aluminium sulfate. A nematicide is a type of chemical pesticide used to kill parasitic nematodes (a phylum of worm). A nematicide is obtained from a neem tree's seed cake; which is the residue of neem seeds after oil extraction. The neem tree is known by several names in the world but was first cultivated in India since ancient times.

Antimicrobials

In the following examples, antimicrobials suitable for agrochemical compositions according to the present invention are given. Bactericidal disinfectants mostly used are those applying active chlorine (i.e., hypochlorites, chloramines, dichloroisocyanurate and trichloroisocyanurate, wet chlorine, chlorine dioxide, etc.), active oxygen (peroxides such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds such as chlorhexidine, glucoprotamine, octenidine dihydrochloride, etc.), strong oxidizers such as ozone and permanganate solutions;

heavy metals and their salts such as colloidal silver, silver nitrate, mercury chloride, phenylmercury salts, copper sulfate, copper oxide-chloride etc. Heavy metals and their salts are the most toxic and environmentally hazardous bactericides and, therefore, their use is strongly suppressed or forbidden; further, also properly concentrated strong acids (phosphoric, nitric, sulfuric, amidosulfuric, toluenesulfonic acids) and alcalis (sodium, potassium, calcium hydroxides) between pH<1 or >13, particularly below elevated temperatures (above 60° C.) kill bacteria.

As antiseptics (i.e., germicide agents that can be used on human or animal body, skin, mucoses, wounds and the like), few of the above mentioned disinfectants can be used under proper conditions (mainly concentration, pH, temperature and toxicity toward man/animal). Among them, important are Some properly diluted chlorine preparations (e.g. Daquin's solution, 0.5% sodium or potassium hypochlorite solution, pH-adjusted to pH 7-8, or 0.5-1% solution of sodium benzenesulfochloramide (chloramine B)), some iodine preparations such as iodopovidone in various galenics (ointments, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid some phenolic compounds such as hexachlorophene, triclosan and Dibromol, and cation-active compounds such as 0.05-0.5% benzalkonium, 0.5-4% chlorhexidine, 0.1-2% octenidine solutions.

Bactericidal antibiotics kill bacteria; bacteriostatic antibiotics only slow down their growth or reproduction. Penicillin is a bactericide, as are cephalosporins. Aminoglycosidic antibiotics can act in both a bactericidic manner (by disrupting cell wall precursor leading to lysis) or bacteriostatic manner (by connecting to 30s ribosomal subunit and reducing translation fidelity leading to inaccurate protein synthesis). Other bactericidal antibiotics according to the present invention include the fluoroquinolones, nitrofurans, vancomycin, monobactams, co-trimoxazole, and metronidazole.

Preferred actives are those with systemic or partially systemic mode of action such as azoxystrobin.

Preferred Uses of the Auxiliary Mixtures

Further embodiments of the present invention refer to concrete uses of the auxiliary composition comprising components (a), (b) and (c) as emulsifiers,
adjuvants,
solvents or solubilisers, or
tank-mix additives
for the production of agrochemical compositions. The auxiliary compositions may be added to the final products in amounts of about 5 to about 50% w/w (concentrates) or about 0.1 to about 1 (diluted formulations).

EXAMPLES

Examples 1 and 2

Comparative Examples C1 and C2

The efficiency of the auxiliary mixtures according to the present invention is demonstrated via the control of Asian Soybean Rust. Field trials were conducted in Brazil. Two standard biocide compositions from the market were applied to soybean crops: "Opera" (BASF) contains 5% w/w epoxiconazole and 13.3% w/w pyraclostrobin, the former is a preventive and curative fungicide, the latter a protectant, curative, and translaminar fungicide. "Folicur" (Bayer CropScience) contains tebuconazole, a fungicide with protective, curative, and eradicant properties. The two compositions were applied at full recommended rate and at a 50% level. These experiments are compared to similar treatment of the plants adding in both cases an auxiliary mixture according to the present invention containing about (A) 75% w/w soybean oil+10 EO, 10% w/w octyl glucoside and 15% w/w tall oil fatty acid and (B) 60% sorbitan-mono/dilaurate+25 EO, 25% w/w decyl glucoside and 15% w/w tall oil fatty acid, both at a concentration of 150 ml/ha. The results are shown in Table 1.

TABLE 1

Soybean Crop Yield influenced by
Asian Soybean Rust-relative to control (= 100)

|  | Examples | Opera | Folicur |
|---|---|---|---|
|  | Control | 100 | 100 |
| Fungicides used at full recommended rate |
| C1 | without additive | 142 | 130 |
| 1a | plus additive A | 158 | 140 |
| 1b | plus additive B | 155 | 142 |
| Fungicides at 50% of the full recommended rate |
| C2 | without additive | 130 | 152 |
| 2a | plus additive A | 138 | 158 |
| 2b | plus additive B | 135 | 156 |

As clearly indicated by the examples and comparative examples adding of the auxiliary agent increases the efficiency of the fungicides significantly.

Example 3

Comparative Example C3

A separate study was undertaken to compare the performance of the invented composition compared with an industry standard, more particularly a crop oil concentrate (COC), on the uptake of nicosulfuron on barnyard grass and green foxtail. Nicosulfuron as Accent WDG 75 was used at 0.031% w/v (46.7 g active ingredient/150 l/ha). Radio-labelled nicosulfuron (50 mCi/mmol) was added to freshly prepared treatment solution 0.5 h prior to use. The $^{14}C$ nicosulfuron comprised 7% by mass. Spray solutions with nicosulfuron alone i.e. without adjuvant, were formulated in 50% acetone. The results are shown in Table 2.

TABLE 2

| Nicosulfuron treatments | | |
|---|---|---|
| Example | Plus adjuvant | Adjuvant rate (% v/v) |
| Control | No adjuvant | 0 |
| 3a | plus additive A | 0.25 |
| 3b | Plus additive B | 0.24 |
| C3 | Crop oil concentrate* | 1.0 |

*The crop oil concentrate (COC) contains 83% oil and 17% emulsifier

Examples 4 to 6

Using five replicates, seeds of barnyard grass and green foxtail were sown at 5 mm depth in pots and kept for up to four weeks at 70% relative humidity and exposed each day for 14 h to about 500 µmol/m² light intensity. Plants were at the 3-5 leaf stage when used for uptake studies, well watered throughout the time until harvest. Droplets were applied about 6 h after the start of the photoperiod. Leaves were sampled 24 h after treatment and the treated surface was washed with water/acteome to recover unabsorbed nicosulfuron. A liquid scintillation counter was used. Foliar uptake was defined as the radioactivity not recovered from washing the treated leaves and was calculated as a percentage of the applied dose. For statistical purposes, analysis of variance and least significant difference (LSD) test were used to compare treatments. The results are shown in Table 3.

TABLE 3

| Uptake of nicosulfuron formulations 24 h after treatment | | |
|---|---|---|
| Example | Barnyard grass | Green foxtail |
| 4 | 81.5 c | 77.0 b |
| 5 | 97.9 a | 96.0 a |
| 6 | 95.7 b | 94.6 a |

Means within species sharing common postscripts are not significantly different (P=0.05)

As shown in Table 3, the uptake of nicosulfuron into two graminaceous species at 24 hours after treatment was increased by either adjuvant. The adjuvant according to this invention provided significantly greater uptake of the herbicide than the COC into barnyard grass at a much lower dose. For green foxtail, uptake by the adjuvant according to this invention was numerically greater than the COC, however, from a statistical point of view not significant at a confidence level of 95%.

What is claimed is:

1. An agrochemical auxiliary composition comprising:
(a) an alkoxylated polyol ester,
(b) an alkyl or alkenyl oligoglycoside, and
(c) a fatty acid or salt thereof;

wherein said alkoxylated polyol ester is an alkoxylated triglyceride according to general formula (I):

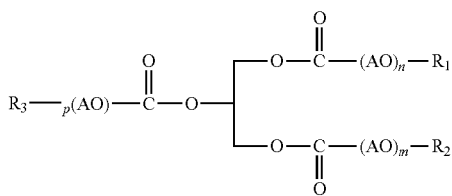

wherein $R_1$, $R_2$, $R_3$ are independently linear or branched, saturated or unsaturated alkyl or hydroxyalkyl residues having 5 to 21 carbon atoms; and n, m, and p are independently 0 or integers of from 1 to 50 with the condition that the sum (m+n+p) is not zero, and AO is an ethylene glycol or propylene glycol unit.

2. The composition of claim 1, wherein said alkoxylated polyol ester (component a) has an HLB value having a range of 2 to 15.

3. The composition of claim 1, wherein said fatty acid (component c) has a general formula (III)

$$R^5CO\text{—}OX \quad \text{(III)}$$

wherein $R^5CO$ represents a linear or branched, saturated or unsaturated acyl radical having 6 to 22 carbon atoms and X stands for hydrogen or an alkaline metal.

4. The composition of claim 1, comprising:
a. 60 to 90% w/w alkoxylated polyol esters
b. 5 to 15% w/w alkyl or alkenyl oligoglycosides, and
c. 5 to 15% w/w fatty acids or their salts.

5. An agrochemical composition comprising
a. an alkoxylated polyol ester,
b. alkyl or alkenyl oligoglycoside,
c. a fatty acid or salt thereof, and
d. a biocide
wherein said alkoxylated polyol ester is an alkoxylated triglyceride according to general formula (I):

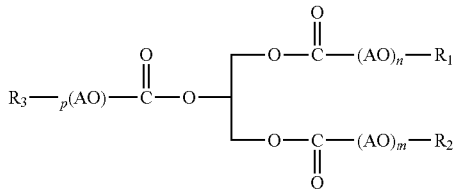

wherein $R_1$, $R_2$, $R_3$ are independently linear or branched, saturated or unsaturated alkyl or hydroxyalkyl residues having 5 to 21 carbon atoms; and n, m, and p are independently 0 or integers of from 1 to 50 with the condition that the sum (m+n+p) is not zero, and AO is an ethylene glycol or propylene glycol unit.

6. A method of producing agrochemical compositions, the method comprising using the composition of claim 1 as an emulsifier for the production of agrochemical compositions.

7. A method of producing agrochemical compositions, the method comprising using the composition of claim 1 as an adjuvant for the production of agrochemical compositions.

8. A method of producing agrochemical compositions, the method comprising using the composition of claim 1 as a solvent or solubiliser for the production of agrochemical compositions.

9. A method of producing agrochemical compositions, the method comprising using the composition of claim 1 as a tank-mix additive for the production of agrochemical compositions.

10. The composition of claim 4, further comprising water.

11. The composition of claim 10, wherein components (a), (b) and (c) and water add up to 100%.

12. The composition of claim 5, wherein the biocide comprises an active ingredient selected from the group consisting of epoxiconazole, pyraclostrobin, tebuconazole, and combinations thereof.

13. The composition of claim 4, wherein said alkyl or alkenyl oligoglycoside is alkoxylated, and is an adduct of, on average, 1 to 20 moles of ethylene oxide or propylene oxide to the free hydroxyl groups of the glycoside.

14. The composition of claim 5, wherein said alkyl or alkenyl oligoglycoside is alkoxylated, and is an adduct of on average 1 to 20 moles of ethylene oxide or propylene oxide to the free hydroxyl groups of the glycoside.

15. An agrochemical auxiliary composition consisting of:
a. an alkoxylated polyol ester,
b. an alkyl or alkenyl oligoglycoside, and
c. a fatty acid or salt thereof;
wherein the alkoxylated polyol ester is present in an amount that is greater than the total amount of the alkyl or alkenyl oligoglycoside and the fatty acid.

16. The agrochemical composition of claim 15, wherein said alkoxylated polyol ester is an alkoxylated triglyceride according to general formula (I):

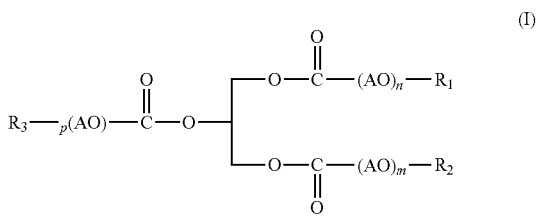

wherein $R_1$, $R_2$, $R_3$ are independently linear or branched, saturated or unsaturated alkyl or hydroxyalkyl residues having 5 to 21 carbon atoms; and n, m, and p are independently 0 or integers of from 1 to 50 with the condition that the sum (m+n+p) is not zero, and AO is an ethylene glycol or propylene glycol unit.

* * * * *